United States Patent
Pallakoff et al.

(10) Patent No.: US 12,340,882 B1
(45) Date of Patent: Jun. 24, 2025

(54) SYSTEMS AND METHODS TO CAUSE ANNOTATION TRANSFERS BETWEEN CLIENT COMPUTING PLATFORMS

(71) Applicant: Suki AI, Inc., Redwood City, CA (US)

(72) Inventors: Matt Pallakoff, Redwood City, CA (US); Luis Daniel Mosquera, Burlingame, CA (US)

(73) Assignee: Suki AI, Inc., Redwood City, CA (US)

( * ) Notice: Subject to any disclaimer, the term of this patent is extended or adjusted under 35 U.S.C. 154(b) by 416 days.

(21) Appl. No.: 17/977,554

(22) Filed: Oct. 31, 2022

(51) Int. Cl.
*G06F 21/33* (2013.01)
*G16H 10/60* (2018.01)

(52) U.S. Cl.
CPC .............. *G16H 10/60* (2018.01); *G06F 21/33* (2013.01)

(58) Field of Classification Search
None
See application file for complete search history.

(56) References Cited

U.S. PATENT DOCUMENTS

| | | | |
|---|---|---|---|
| 2013/0072170 A1* | 3/2013 | Hong | H04L 67/51 455/414.1 |
| 2013/0290872 A1* | 10/2013 | Hong | G06F 40/169 715/753 |
| 2020/0004810 A1* | 1/2020 | Manber | G06F 3/0482 |

* cited by examiner

*Primary Examiner* — Rayeez R Chowdhury
(74) *Attorney, Agent, or Firm* — Esplin & Associates, PC (57) ABSTRACT

Systems and methods to cause annotation transfers between client computing platforms are disclosed. Exemplary implementations may: manage user account information within user accounts associated with users; authenticate a first device and a second device to a first user account based on first login information; receive, via a network from the first device, a first annotation; transmit, to the second device responsive to receipt of the first annotation, a transfer indication that the first annotation is to be inserted into a document being presented via the second device; receive, responsive to the transfer indication, a point of insertion within the document; effectuate, via the first device, presentation of a completion request to complete the insertion; receive, from the first device responsive to presentation of the completion request, a completion indication to cause the first annotation to be inserted; effectuate, responsive to reception of the completion indication, insertion of the first annotation.

20 Claims, 5 Drawing Sheets

SYSTEMS AND METHODS TO CAUSE ANNOTATION TRANSFERS BETWEEN CLIENT COMPUTING PLATFORMS

FIELD OF THE DISCLOSURE

The present disclosure relates to systems and methods to cause annotation transfers between client computing platforms.

BACKGROUND

Doctors or other users of annotation systems are typically required to manually transfer content of an annotation from a platform where they generated the annotation with into a target location, such as an electronic medical record (EMR). Manually transferring the content of the annotation may include opening the annotation on a web application of the platform they generated the annotation with on a web browser of a desktop computer, and copying and pasting each section of the annotation from the web application to the target location accessed via an application of a target platform on the desktop computer, such as the EMR accessed via an EMR application on the desktop computer. This tedious manual transfer may still be preferred over directly generating the annotation via the application on the desktop (e.g., the EMR application).

SUMMARY

One aspect of the present disclosure relates to a system configured to cause annotation transfers between client computing platforms. A first client computing platform and a second client computing platform both associated with a user may be authenticated to a user account of the user based on login information included in user account information managed by the system. The user may indicate via the first client computing platform that they want to transfer an annotation from the first client computing platform to a second client computing platform. The system, a backend infrastructure, may receive this indication and enable the user to provide a point of insertion within a document presented via the second client computing platform and complete insertion of the annotation at the point of insertion via the first client computing platform. Such implementation, and variation thereof described herein, may eliminate requiring the user to download and/or log into a web application variation of a platform that the user initially used, via the first client computing platform, to generate the annotation on the second client computing platform, and subsequently manually copying and pasting one or more portions of the annotations to the document. Therefore, communication of annotations to create or update documents managed via the second client computing platform may be streamlined to provide speed and efficiency.

The system may include one or more hardware processors configured by machine-readable instructions. The machine-readable instructions may include one or more instruction components. The instruction components may include computer program components. The instruction components may include one or more of account management component, annotation receiving component, indication component, insertion component, presentation component, and/or other instruction components.

The account management component may be configured to manage user account information within user accounts associated with users that access a system that is configured to cause annotation transfers between client computing platforms via client computing platforms. The user account information may include login information, annotation templates, and/or other information. The user accounts may include a first user account associated with a first user. The user account information within the first user account may include first login information and one or more annotation templates.

The account management component may be configured to authenticate a first client computing platform to the first user account based on the first login information included in the first account. The account management component may be configured to authenticate a second client computing platform to the first user account based on the first login information included in the first user account.

The annotation receiving component may be configured to receive, via a network from the first client computing platform, a first annotation and store in electronic storage.

The indication component may be configured to transmit, to the second client computing platform responsive to receipt of the first annotation, a transfer indication. The transfer indication may convey that the first annotation is to be inserted, from the electronic storage, into a document being presented to the first user via the second client computing platform.

The insertion component may be configured to receive, responsive to the transfer indication, a point of insertion within the document being presented to the first user via the second client computing platform.

The presentation component may be configured to effectuate, via the first client computing platform responsive to receipt of the point of insertion, presentation of a completion request to complete the insertion of the first annotation at the point of insertion.

The insertion component may be further configured to receive, from the first client computing platform responsive to presentation the completion request, a completion indication to cause the first annotation to be inserted into the document at the point of insertion from the electronic storage. The insertion component may be configured to effectuate, responsive to reception of the completion indication, insertion of the first annotation within the document being presented to the first user via the second client computing platform at the point of insertion.

As used herein, the term "obtain" (and derivatives thereof) may include active and/or passive retrieval, determination, derivation, transfer, upload, download, submission, and/or exchange of information, and/or any combination thereof. As used herein, the term "effectuate" (and derivatives thereof) may include active and/or passive causation of any effect, both local and remote. As used herein, the term "determine" (and derivatives thereof) may include measure, calculate, compute, estimate, approximate, generate, and/or otherwise derive, and/or any combination thereof.

These and other features, and characteristics of the present technology, as well as the methods of operation and functions of the related elements of structure and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for the purpose of illustration and description only and are not intended as a definition of the limits of the invention. As used in the specification and in the claims, the singular form of 'a', 'an', and 'the' include plural referents unless the context clearly dictates otherwise.

DETAILED DESCRIPTION

Figure 1:
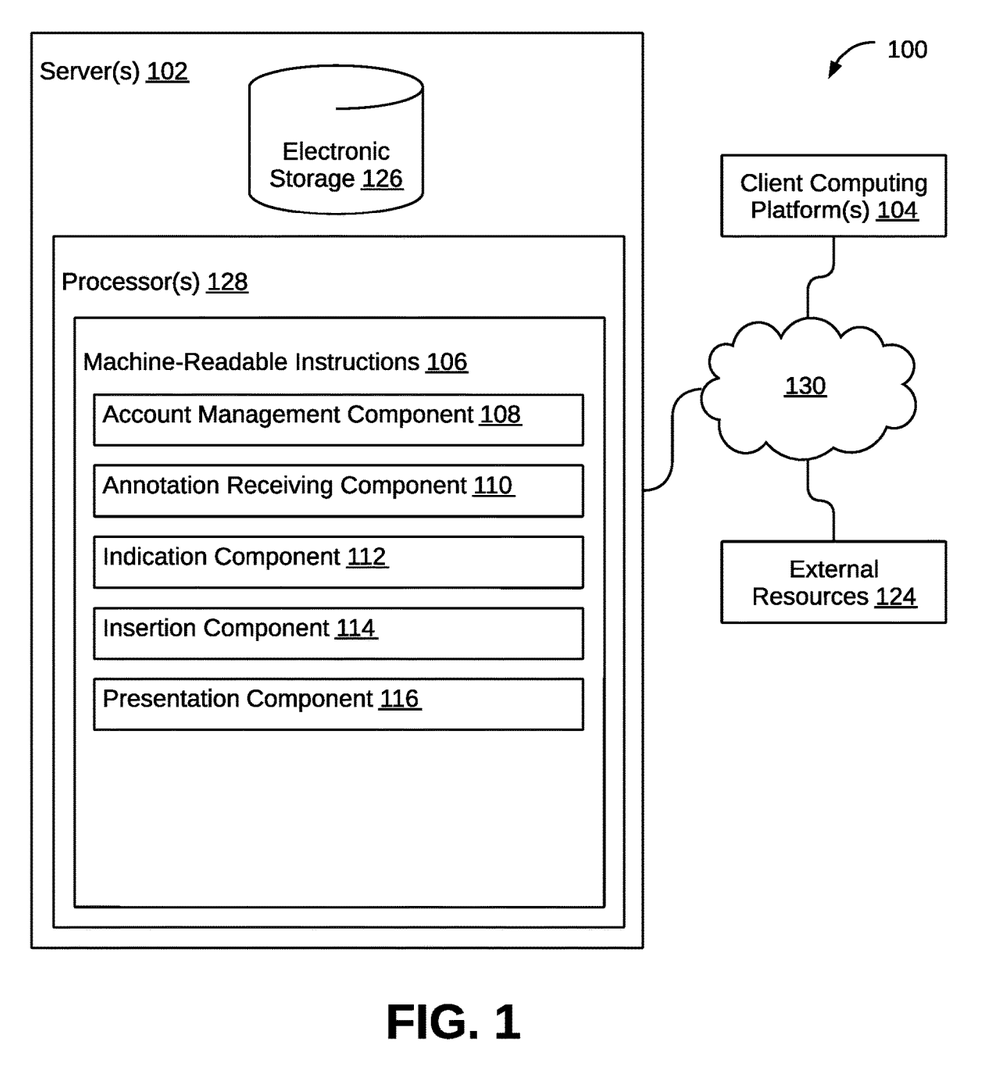
FIG. 1 illustrates a system configured to cause annotation transfers between client computing platforms, in accordance with one or more implementations.

FIG. 1 illustrates a system 100 configured to cause annotation transfers between client computing platforms, in accordance with one or more implementations. In some implementations, system 100 may include one or more servers 102. Server(s) 102 may be configured to communicate with one or more client computing platforms 104 according to a client/server architecture and/or other architectures. Client computing platform(s) 104 may be configured to communicate with other client computing platforms via server(s) 102 and/or according to a peer-to-peer architecture and/or other architectures. Users may access system 100 via client computing platform(s) 104.

Server(s) 102 may be configured by machine-readable instructions 106. Machine-readable instructions 106 may include one or more instruction components. The instruction components may include computer program components. The instruction components may include one or more of account management component 108, annotation receiving component 110, indication component 112, insertion component 114, presentation component 116, and/or other instruction components.

Account management component 108 may be configured to manage user account information within user accounts associated with users that access system 100 configured to cause annotation transfers between client computing platforms 104 via client computing platforms 104. The annotations may include notes taken on individual client computing platforms 104, documents or records created via client computing platforms 104, sections of the documents or records, edits to individual ones of the documents and/or sections thereof, and/or other annotations. The user accounts may represent different users of system 100 and/or other systems integrated with system 100 (e.g., electronic medical record (EMR) management systems). The user account information may include login information, user information, annotation templates, and/or other information. The login information may include a username, a first name, a last name, an email address, a password, one or more security questions and answers, and/or other login information that facilitates with authentication of a given user on multiple client computing platforms 104. The user information for individual ones of the users may identify the individual users. The user information may include the first name, the last name, a role, one or more supervisors, one or more care facilities, a field of a given profession (e.g., a field of medicine), education (e.g., degrees, schools attended), certifications, the email address, the password, and/or other user information.

The annotation templates may be outlines that the users may use to generate the annotations based on. In some implementations, the annotation templates may be unique to the individual users and their associated user account information. Such annotation templates may thus be modified by the users. In some implementations, the annotation templates may be globally the same for all the user account information of the users of system 100.

By way of non-limiting example, the user accounts may include a first user account associated with a first user and/or other user accounts associated with other users. The user account information within the first user account may include first login information, one or more annotation templates, and/or other information.

Account management component 108 may be configured to authenticate a first client computing platform 104 to the first user account based on the first login information included in the first user account. Further, account management component 108 may be configured to authenticate a second client computing platform 104 to the first user account based on the first login information included in the first user account. The authentication of first client computing platform 104, second client computing platform 104, and/or other client computing platforms 104 to the first user account may include comparing input login information input by the user via the individual client computing platforms 104 and the first login information included in the first user account. In some implementations, the authentication may include comparing the input login information with the first login information and determining whether a particular amount of the first login information, a majority of the first login information, and/or particular elements that comprise the first login information are input by the first user and verified against the first login information.

In some implementations, first client computing platform 104 may be a mobile smart phone or other client computing platform 104 that is portable. Second client computing platform 104 may be a desktop computer, a laptop computer, or other client computing platform 104 that is separate and distinct from first client computing platform 104. Client computing platforms 104 may include an audio section configured to receive audio input (e.g., voice commands) and provide sound feedback (e.g., alerts, notifications, playback). The audio section may include an audio input sensor, such as a microphone, and an audio output device, such as one or more speakers.

Annotation receiving component 110 may be configured to receive, via a network 130 from first client computing platform 104, one or more annotations and store the one or more annotations in electronic storage 126 and/or other storage media. For example, a first annotation may be received from first client computing platform 104 and stored in electronic storage 126. In some implementations, the one or more annotations may be received by annotation receiving component 110 individually subsequent to the authentication of first client computing platform 104. In some implementations, the one or more annotations may be received by annotation receiving component 110 collectively, e.g., all annotations created within a given record via first client computing platform 104 are received, subsequent to the authentication of first client computing platform 104. Annotation receiving component 110 may receive an indication of a selection of user interface element(s) and/or an indication of an utterance of voice command(s) upon first client computing platform 104 detecting the utterance and responsively, receive the one or more annotations. The voice command(s) may be received via first client computing platform 104, second client computing platform 104, or both.

In some implementations, receiving the one or more annotations may be responsive to the user selecting the user interface element(s) presented via first client computing platform 104. The user interface elements presented via client computing platforms 104 may be configured to be selected by the users to cause actions or provide input, such as transmitting the first annotation to annotation receiving component 110. The user interface elements may be configured to facilitate user interaction with the user interface, user entry, and/or selection. By way of non-limiting illustration, the user interface elements may include one or more of text input fields, drop down menus, check boxes, display windows, virtual buttons, and/or other user interface elements.

In some implementations, individual user interface elements may be associated with individual annotation sections created within the given record via first client computing platform 104 and cause transmission of the associated annotation section upon selection of the individual user interface elements. In some implementations, a single user interface element may be associated with the entire given record created via first client computing platform 104 and cause transmission of the entire record upon selection. In some implementations, individual ones of the annotation sections or more than one annotation section of the given record may be highlighted or otherwise featured, such as by the user selecting the annotation section or scrolling to feature the annotation section via first client computing platform 104, and the single user interface element may be selected to cause transmission of the featured annotation section.

In some implementations, receiving the one or more annotations may be responsive to first client computing platform 104 receiving voice commands uttered by the user. A voice command, e.g., "Suki, transfer history section", may command first client computing platform 104 to transmit the first annotation, e.g., population of historical information in a history section of the given record via first client computing platform 104, to annotation receiving component 110. Subsequently, the user may utter an additional different voice command, e.g., "Suki, transfer the vitals," so that a second annotation that is different and separate from the first annotation is received and stored by annotation receiving component 110. In some implementations, the user may utter a third command such as "Suki, transfer everything" so that a multiple annotations, whether multiple different records or multiple different sections of the given record, are received and stored by annotation receiving component 110.

Indication component 112 may be configured to transmit, to second client computing platform 104, a transfer indication. The transfer indication may indicate that the one or more annotations are to be inserted, from electronic storage 126, into a document, a record, or text box being presented to the first user via second client computing platform 104. The transfer indication may be transmitted by indication component 112 responsive to receipt of the one or more annotations by annotation receiving component 110. The transfer indication may initiate and enable selection of a point of insertion by the first user via second client computing platform 104. Initiating the selection of the point of insertion may include emphasizing a cursor (e.g., enlarging the cursor, flashing the cursor, moving the cursor, etc.), effectuating a noise via second client computing platform 104, and/or other initiation emphasis. The cursor may be native to second client computing platform 104 and facilitate with selection of elements presented via second client computing platform 104. In some implementations, initiating the selection of the point of insertion may include effectuating presentation of an insertion point prompt via first client computing platform 104. The prompt may inform the first use to provide the point of insertion via the second client computing platform 104. In some implementations, the document may be a particular electronic medical record (e.g., for a particular patient) and/or other record managed by a documentation system running on second client computing platform 104 that the first user may authenticate to the first user account based on the first login information. In some implementations, the text box may be for a particular section or portion of the particular electronic medical record or the other record.

Insertion component 114 may be configured to receive the point of insertion within the document being presented to the first user via second client computing platform 104. The points of insertion may be where the one or more annotations are to be inserted. The point of insertion may be received responsive to the transfer indication. In some implementations, the point of insertion may be a particular section of the document. In some implementations, the point of insertion may be a blank document. In some implementations, the document may one of the annotation templates.

In some implementations, the point of insertion may be determined upon the cursor being located at the point of insertion for a particular amount of time (e.g., five seconds). The particular amount of time may be fixed, or modifiable by the first user and/or other users (e.g., an administrative user of system 100). In some implementations, the point of insertion may be determined upon detection of a touch selection by the first user on a touchscreen of second client computing platform 104. The touch selection may be performed with a finger of the first user, a stylus, and/or other tool. The touch selection may be a particular pattern fixed by system 100, or modifiable by the first user and/or other users. For example, the pattern may include a single tap, a double tap, a tap and holding for a particular amount of time (e.g., three seconds), and/or other patterns. In some implementations, the point of insertion may be determined based on an utterance by the user specifying such. For example, the first user may utter "Suki, in the History section" or "Suki, at the beginning of the document."

Presentation component 116 may be configured to effectuate presentation of a completion request. The completion request may request the first user to complete the insertion of the one or more annotations at the point of insertion. The completion request may be presented to the first user via first client computing platform 104 responsive to receipt of the point of insertion. The completion request may include a completion prompt, a second user interface element, and/or other elements that convey the completion request. The completion prompt, for example, may inform the first user that they need to vocally and/or manually complete the insertion by uttering a second voice command (e.g., "Suki, complete transfer") and/or by selecting the second user interface element, respectively.

Insertion component 114 may be configured to receive a completion indication to cause the one or more annotations to be inserted into the document at the point of insertion from electronic storage 126. The completion indication may be received from first client computing platform 104 responsive to presentation the completion request. The completion indication may confirm that the insertion of the one or more annotations may occur. In some implementations, receiving the completion indication may include receiving an indication of the selection of the second user interface element presented via first client computing platform 104 to cause the one or more annotations to be inserted into the document at the point of insertion from electronic storage 126. In some implementations, receiving the completion indication may include receiving the second voice command via first client computing platform 104 to cause the one or more annotations to be inserted into the document at the point of insertion from electronic storage 126.

Insertion component 114 may be configured to effectuate insertion of the one or more annotations within the document being presented to the first user via second client computing platform 104 at the point of insertion. The insertion may be effectuated responsive to reception of the completion indication. In some implementations, presentation component 116 may be configured to effectuate presentation of the insertion of the one or more annotations at point of insertion in the document via second client computing platform 104 while the insertion occurs.

In some implementations where multiple annotations are to be transferred individually, for example the second annotation subsequent to the first annotation or other annotations, the receipt of the second annotations, transmission of a second transfer indication, receipt of a second point of insertion, effectuation presentation of a second completion request, receipt of a second completion indication, and effectuation of insertion of the second annotation at the second point of insertion may occur subsequently in a similar manner as described herein. As such, in some implementations, only individual points of insertion via second client computing platform 104 and a single voice command for each transfer are required from the user subsequent to a single authentication of first client computing platform 104 and second client computing platform 104.

By contrast, existing graphical user interfaces (GUI) may require the user to provide the point of insertion in a target document via second client computing platform 104, then open a document annotation created on first client computing platform 104, scroll through its section annotations, indicate a section annotation they want to transfer, and utter a voice command such as "Suki, transfer section one" to transfer just that section annotation. Furthermore, the user may be required to subsequently provide another point of insertion in the target document via second client computing platform 104 to transfer a second section annotation, then reopen the document annotation via first client computing platform 104 (if it's not still open), scroll through the section annotations again to indicate the second annotation section they want to transfer, and utter a voice command such as "Suki, transfer section two" to transfer the second annotation section, and so on for other annotation section transfers. Such existing technique requires more from the user and more reception of information than system 100 described herein.

Figure 3A:
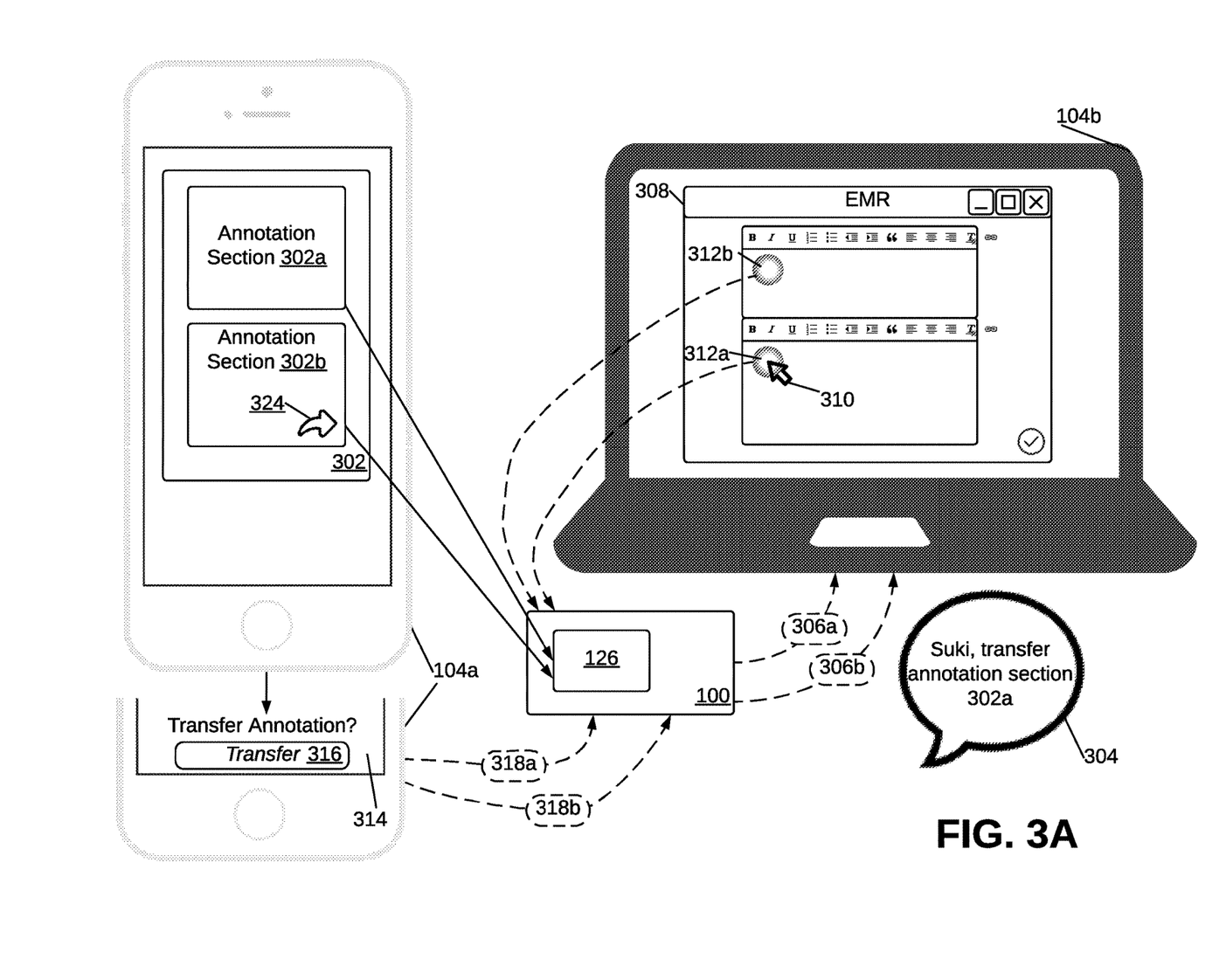
FIG. 3A-C illustrates an example implementation of the system configured to cause annotation transfers between client computing platforms, in accordance with one or more implementations.
Figure 3B:
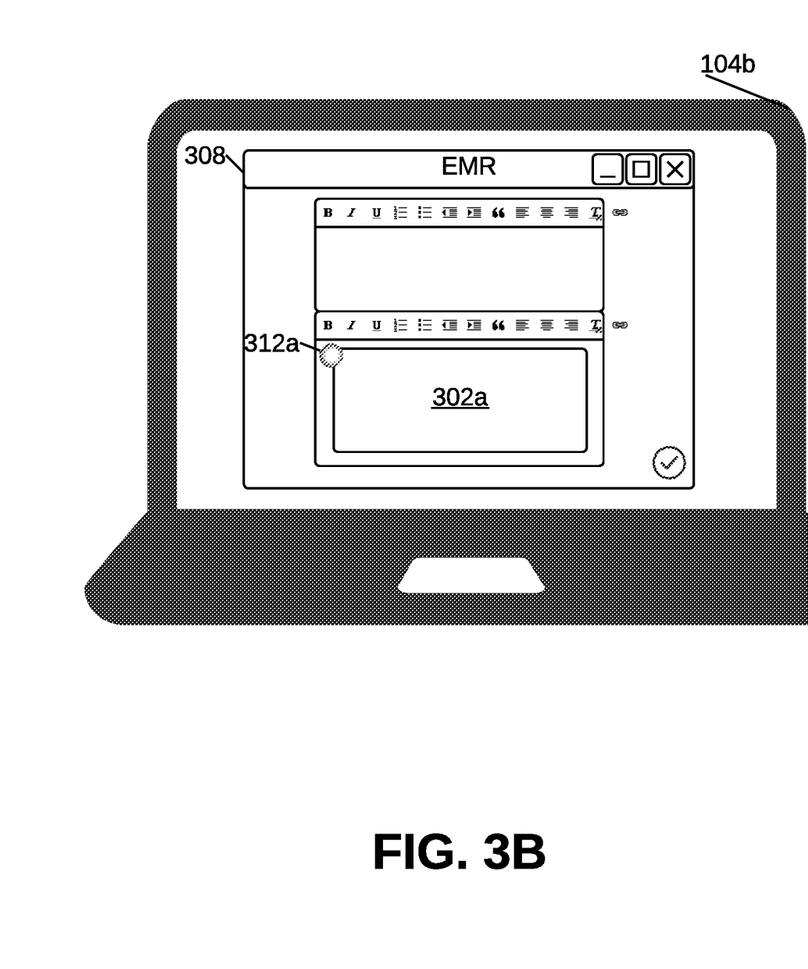

FIG. 3A illustrates a client computing platform 104*a* and a client computing platform 104*b* both of which are authenticated to a user account of a user based on login information included in the user account (not illustrated). The user may have generated annotation sections 302*a* and 302*b* within a document 302 on client computing platform 104*a*. To initiate transfer of annotation sections 302*a* and/or 302*b* to client computing platform 104*b*, the user may utter voice command 304 to transmit annotation section 302*a* via client computing platform 104*a*. Upon utterance of voice command 304, annotation section 302*a* may be transmitted to system 100 and store in electronic storage 126 of system 100 (the same as in FIG. 1). A transfer indication 306*a* may be transmitted from system 100 to client computing platform 104*b* indicating that annotation section 302*a* is to be inserted at some point of insertion presented on client computing platform 104*b* to the user. The user may move a cursor 310 of client computing platform 104*b* to a point of insertion 312*a* within a document 308 where annotation section 302*a* is to be inserted. Point of insertion 312*a* may be transmitted to system 100, and subsequently, a completion request 314 requesting completion of the insertion of an annotation at a given point of insertion may be presented via client computing platform 104*a*, such as annotation section 302*a* at point of insertion 312*a*, or other annotations at other points of insertion. Completion request 314 may include a user interface element 316 that the user may select to provide a completion indication 318*a* to system 100 indicating that completion of the insertion of annotation section 302*a* may occur. Referring to FIG. 3B in addition to FIG. 3A, receipt of completion indication 318*a* by system 100 may cause annotation section 302*a* to be inserted into document 308 from electronic storage 126, as illustrated in FIG. 3B, at point of insertion 312*a*.

Figure 3C:
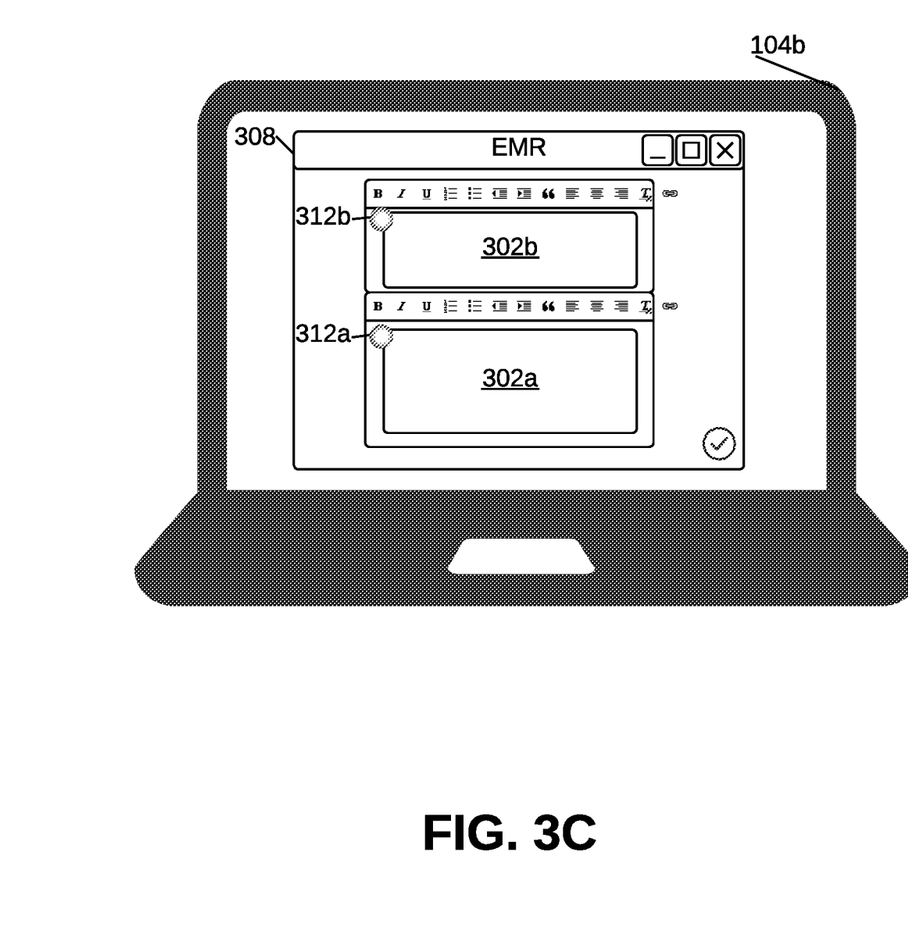

Referring back to FIG. 3A, to subsequently initiate transfer of annotation section 302*b* to client computing platform 104*b*, the user may either utter a second voice command similar to voice command 304, or select user interface element 324 presented via client computing platform 104*a* in association with annotation section 302*b*. Upon section of user interface element 324, annotation section 302*b* may be transmitted to system 100 and store in electronic storage 126 of system 100 (the same as in FIG. 1). A transfer indication 306*b* may be transmitted from system 100 to client computing platform 104*b* indicating that annotation section 302*b* is to be inserted at some point of insertion presented on client computing platform 104*b* to the user. The user may move cursor 310 of client computing platform 104*b* from point of insertion 312*a* to a point of insertion 312*b* within document 308 where annotation section 302*b* is to be inserted. Point of insertion 312*b* may be transmitted to system 100, and subsequently, completion request 314 requesting completion of the insertion of annotation section 302*b* at point of insertion 312*b* may be re-presented via client computing platform 104*a*. Similarly, the user may select user interface element 316 to provide a completion indication 318*b* to system 100 indicating that completion of the insertion of annotation section 302*b* may occur. Referring to FIG. 3C in addition to FIG. 3A, receipt of completion indication 318*b* by system 100 may cause annotation section 302*b* to be inserted into document 308 from electronic storage 126, as illustrated in FIG. 3C, at point of insertion 312*b*.

Referring back to FIG. 1, in some implementations, server(s) 102, client computing platform(s) 104, and/or external resources 124 may be operatively linked via one or more electronic communication links. For example, such electronic communication links may be established, at least in part, via network 130 such as the Internet and/or other networks. It will be appreciated that this is not intended to be limiting, and that the scope of this disclosure includes implementations in which server(s) 102, client computing platform(s) 104, and/or external resources 124 may be operatively linked via some other communication media.

A given client computing platform 104 may include one or more processors configured to execute computer program components. The computer program components may be configured to enable an expert or user associated with the given client computing platform 104 to interface with system 100 and/or external resources 124, and/or provide other functionality attributed herein to client computing platform(s) 104. By way of non-limiting example, the given client computing platform 104 may include one or more of a desktop computer, a laptop computer, a handheld computer, a tablet computing platform, a NetBook, a Smartphone, a gaming console, and/or other computing platforms.

External resources 124 may include sources of information outside of system 100, external entities participating with system 100, and/or other resources. In some implementations, some or all of the functionality attributed herein to external resources 124 may be provided by resources included in system 100.

Server(s) 102 may include electronic storage 126, one or more processors 128, and/or other components. Server(s) 102 may include communication lines, or ports to enable the exchange of information with network 130 and/or other computing platforms. Illustration of server(s) 102 in FIG. 1 is not intended to be limiting. Server(s) 102 may include a plurality of hardware, software, and/or firmware components operating together to provide the functionality attributed herein to server(s) 102. For example, server(s) 102 may be implemented by a cloud of computing platforms operating together as server(s) 102.

Electronic storage 126 may comprise non-transitory storage media that electronically stores information. The electronic storage media of electronic storage 126 may include one or both of system storage that is provided integrally (i.e., substantially non-removable) with server(s) 102 and/or removable storage that is removably connectable to server(s) 102 via, for example, a port (e.g., a USB port, a firewire port, etc.) or a drive (e.g., a disk drive, etc.). Electronic storage 126 may include one or more of optically readable storage media (e.g., optical disks, etc.), magnetically readable storage media (e.g., magnetic tape, magnetic hard drive, floppy drive, etc.), electrical charge-based storage media (e.g., EEPROM, RAM, etc.), solid-state storage media (e.g., flash drive, etc.), and/or other electronically readable storage media. Electronic storage 126 may include one or more virtual storage resources (e.g., cloud storage, a virtual private network, and/or other virtual storage resources). Electronic storage 126 may store software algorithms, information determined by processor(s) 128, information received from server(s) 102, information received from client computing platform(s) 104, and/or other information that enables server(s) 102 to function as described herein.

Processor(s) 128 may be configured to provide information processing capabilities in server(s) 102. As such, processor(s) 128 may include one or more of a digital processor, an analog processor, a digital circuit designed to process information, an analog circuit designed to process information, a state machine, and/or other mechanisms for electronically processing information. Although processor(s) 128 is shown in FIG. 1 as a single entity, this is for illustrative purposes only. In some implementations, processor(s) 128 may include a plurality of processing units. These processing units may be physically located within the same device, or processor(s) 128 may represent processing functionality of a plurality of devices operating in coordination. Processor(s) 128 may be configured to execute components 108, 110, 112, 114, and/or 116, and/or other components. Processor(s) 128 may be configured to execute components 108, 110, 112, 114, and/or 116, and/or other components by software; hardware; firmware; some combination of software, hardware, and/or firmware; and/or other mechanisms for configuring processing capabilities on processor(s) 128. As used herein, the term "component" may refer to any component or set of components that perform the functionality attributed to the component. This may include one or more physical processors during execution of processor readable instructions, the processor readable instructions, circuitry, hardware, storage media, or any other components.

It should be appreciated that although components 108, 110, 112, 114, and/or 116 are illustrated in FIG. 1 as being implemented within a single processing unit, in implementations in which processor(s) 128 includes multiple processing units, one or more of components 108, 110, 112, 114, and/or 116 may be implemented remotely from the other components. The description of the functionality provided by the different components 108, 110, 112, 114, and/or 116 described below is for illustrative purposes, and is not intended to be limiting, as any of components 108, 110, 112, 114, and/or 116 may provide more or less functionality than is described. For example, one or more of components 108, 110, 112, 114, and/or 116 may be eliminated, and some or all of its functionality may be provided by other ones of components 108, 110, 112, 114, and/or 116. As another example, processor(s) 128 may be configured to execute one or more additional components that may perform some or all of the functionality attributed below to one of components 108, 110, 112, 114, and/or 116.

Figure 2:
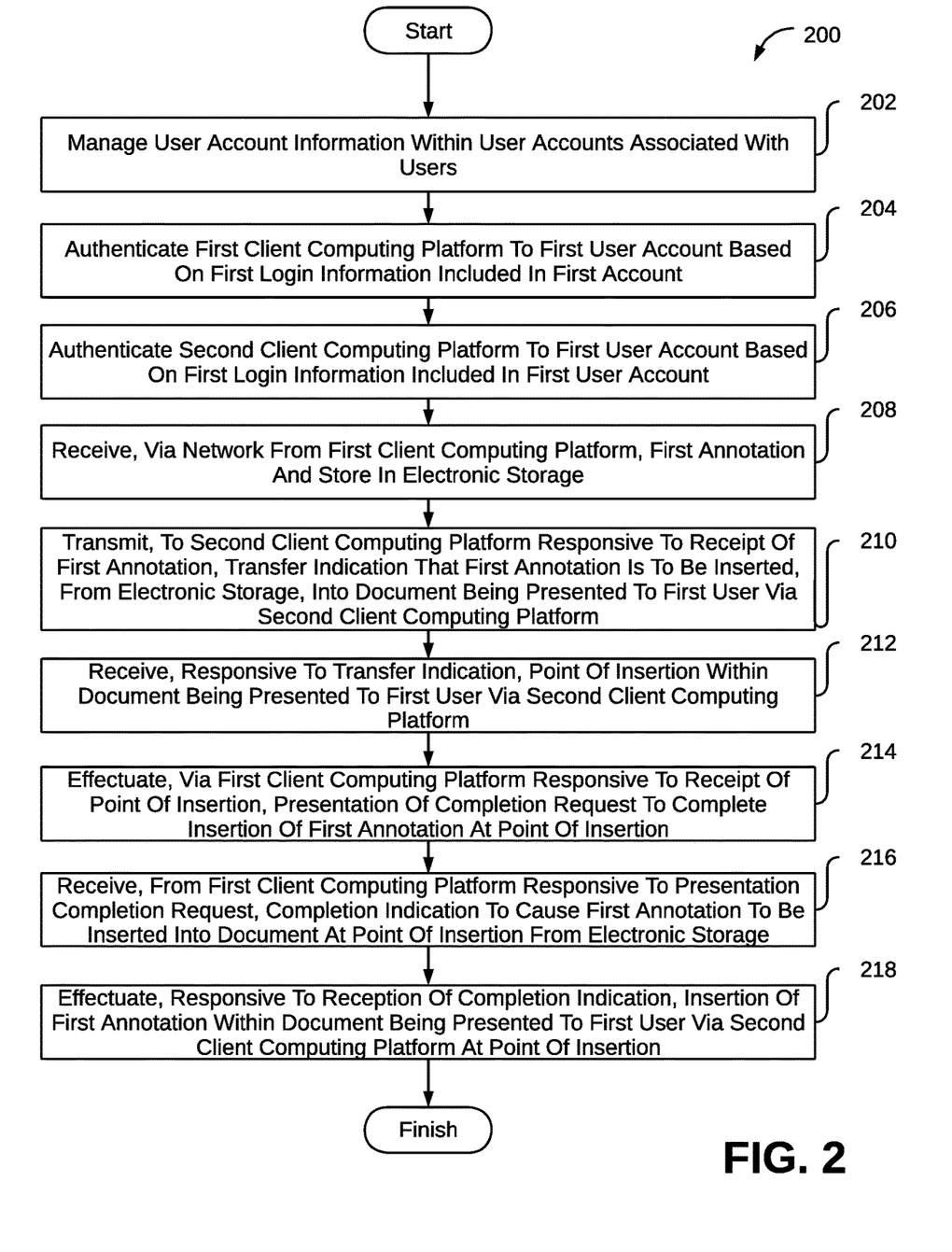
FIG. 2 illustrates a method to cause annotation transfers between client computing platforms, in accordance with one or more implementations.

FIG. 2 illustrates a method 200 to cause annotation transfers between client computing platforms, in accordance with one or more implementations. The operations of method 200 presented below are intended to be illustrative. In some implementations, method 200 may be accomplished with one or more additional operations not described, and/or without one or more of the operations discussed. Additionally, the order in which the operations of method 200 are illustrated in FIG. 2 and described below is not intended to be limiting.

In some implementations, method 200 may be implemented in one or more processing devices (e.g., a digital processor, an analog processor, a digital circuit designed to process information, an analog circuit designed to process information, a state machine, and/or other mechanisms for electronically processing information). The one or more processing devices may include one or more devices executing some or all of the operations of method 200 in response to instructions stored electronically on an electronic storage medium. The one or more processing devices may include one or more devices configured through hardware, firmware, and/or software to be specifically designed for execution of one or more of the operations of method 200.

An operation 202 may include managing user account information within user accounts associated with users that access a system that is configured to cause annotation transfers between client computing platforms via client computing platforms. The user account information within a first user account may include first login information and one or more annotation templates. Operation 202 may be performed by one or more hardware processors configured by machine-readable instructions including a component that is the same as or similar to account management component 108, in accordance with one or more implementations.

An operation 204 may include authenticating a first client computing platform to the first user account based on the first login information included in the first account. Operation 204 may be performed by one or more hardware processors configured by machine-readable instructions including a component that is the same as or similar to account management component 108, in accordance with one or more implementations.

An operation 206 may include authenticating a second client computing platform to the first user account based on the first login information included in the first user account. Operation 206 may be performed by one or more hardware processors configured by machine-readable instructions including a component that is the same as or similar to account management component 108, in accordance with one or more implementations.

An operation 208 may include receiving, via a network from the first client computing platform, a first annotation and store in electronic storage. Operation 208 may be performed by one or more hardware processors configured by machine-readable instructions including a component that is the same as or similar to annotation receiving component 110, in accordance with one or more implementations.

An operation 210 may include transmitting, to the second client computing platform responsive to receipt of the first annotation, a transfer indication that the first annotation is to be inserted, from the electronic storage, into a document being presented to the first user via the second client computing platform. Operation 210 may be performed by one or more hardware processors configured by machine-readable instructions including a component that is the same as or similar to indication component 112, in accordance with one or more implementations.

An operation 212 may include receiving, responsive to the transfer indication, a point of insertion within the document being presented to the first user via the second client computing platform. Operation 212 may be performed by one or more hardware processors configured by machine-readable instructions including a component that is the same as or similar to insertion component 114, in accordance with one or more implementations.

An operation 214 may include effectuating, via the first client computing platform responsive to receipt of the point of insertion, presentation of a completion request to complete the insertion of the first annotation at the point of insertion. Operation 214 may be performed by one or more hardware processors configured by machine-readable instructions including a component that is the same as or similar to presentation component 116, in accordance with one or more implementations.

An operation 216 may include receiving, from the first client computing platform responsive to presentation the completion request, a completion indication to cause the first annotation to be inserted into the document at the point of insertion from the electronic storage. Operation 216 may be performed by one or more hardware processors configured by machine-readable instructions including a component that is the same as or similar to insertion component 114, in accordance with one or more implementations.

An operation 218 may include effectuating, responsive to reception of the completion indication, insertion of the first annotation within the document being presented to the first user via the second client computing platform at the point of insertion. Operation 218 may be performed by one or more hardware processors configured by machine-readable instructions including a component that is the same as or similar to insertion component 114, in accordance with one or more implementations.

Although the present technology has been described in detail for the purpose of illustration based on what is currently considered to be the most practical and preferred implementations, it is to be understood that such detail is solely for that purpose and that the technology is not limited to the disclosed implementations, but, on the contrary, is intended to cover modifications and equivalent arrangements that are within the spirit and scope of the appended claims. For example, it is to be understood that the present technology contemplates that, to the extent possible, one or more features of any implementation can be combined with one or more features of any other implementation.

What is claimed is:

1. A system configured to cause annotation transfers between client computing platforms, the system comprising:
   electronic storage that stores at least annotations; and
   one or more physical processors configured by machine-readable instructions to:
   manage user account information within user accounts associated with users that access the system via the client computing platforms, the user account information including login information and annotation templates, wherein the user accounts include a first user account associated with a first user, the user account information within the first user account including first login information and one or more annotation templates;
   authenticate a first client computing platform to the first user account based on the first login information included in the first user account;
   authenticate a second client computing platform to the first user account based on the first login information included in the first user account;
   receive, via a network from the first client computing platform, a first annotation and store in the electronic storage;
   transmit, to the second client computing platform responsive to receipt of the first annotation, a transfer indication that the first annotation is to be inserted, from the electronic storage, into a document being presented to the first user via the second client computing platform;
   receive, responsive to the transfer indication, a point of insertion within the document being presented to the first user via the second client computing platform;
   effectuate, via the first client computing platform responsive to receipt of the point of insertion, presentation of a completion request to complete the insertion of the first annotation at the point of insertion;
   receive, from the first client computing platform responsive to presentation of the completion request, a completion indication to cause the first annotation to be inserted into the document at the point of insertion from the electronic storage; and
   effectuate, responsive to reception of the completion indication, insertion of the first annotation within the document being presented to the first user via the second client computing platform at the point of insertion.

2. The system of claim 1, wherein receiving the first annotation is responsive to the user selecting a user interface element presented via the first client computing platform.

3. The system of claim 1, wherein receiving the first annotation is responsive to the first client computing platform receiving a voice command uttered by the user.

4. The system of claim 1, wherein receiving the completion indication includes receiving an indication of a selection of a second user interface element presented via the first client computing platform.

5. The system of claim 1, wherein receiving the completion indication includes receiving a second voice command via the first client computing platform to cause the first annotation to be inserted into the document at the point of insertion from the electronic storage.

6. The system of claim 1, wherein the document is a particular electronic medical record.

7. The system of claim 1, wherein the point of insertion is determined upon a cursor being located at the point of insertion for a particular amount of time.

8. The system of claim 1, wherein the insertion of the first annotation at point of insertion in the document is presented via the second client computing platform.

9. The system of claim 1, wherein the first client computing platform is a mobile smart phone.

10. The system of claim 1, wherein the second client computing platform is a desktop computer or a laptop computer.

11. A method to cause annotation transfers between client computing platforms, the method comprising:

managing user account information within user accounts associated with users that access a system that is configured to cause annotation transfers between the client computing platforms via the client computing platforms, the user account information including login information and annotation templates, wherein the user accounts include a first user account associated with a first user, the user account information within the first user account including first login information and one or more annotation templates;

authenticating a first client computing platform to the first user account based on the first login information included in the first user account;

authenticating a second client computing platform to the first user account based on the first login information included in the first user account;

receiving, via a network from the first client computing platform, a first annotation and storing in electronic storage;

transmitting, to the second client computing platform responsive to receipt of the first annotation, a transfer indication that the first annotation is to be inserted, from the electronic storage, into a document being presented to the first user via the second client computing platform;

receiving, responsive to the transfer indication, a point of insertion within the document being presented to the first user via the second client computing platform;

effectuating, via the first client computing platform responsive to receipt of the point of insertion, presentation of a completion request to complete the insertion of the first annotation at the point of insertion;

receiving, from the first client computing platform responsive to presentation of the completion request, a completion indication to cause the first annotation to be inserted into the document at the point of insertion from the electronic storage; and effectuating, responsive to reception of the completion indication, insertion of the first annotation within the document being presented to the first user via the second client computing platform at the point of insertion.

12. The method of claim 11, wherein receiving the first annotation is responsive to the user selecting a user interface element presented via the first client computing platform.

13. The method of claim 11, wherein receiving the first annotation is responsive to the first client computing platform receiving a voice command uttered by the user.

14. The method of claim 11, wherein receiving the completion indication includes receiving an indication of a selection of a second user interface element presented via the first client computing platform.

15. The method of claim 11, wherein receiving the completion indication includes receiving a second voice command via the first client computing platform to cause the first annotation to be inserted into the document at the point of insertion from the electronic storage.

16. The method of claim 11, wherein the document is a particular electronic medical record.

17. The method of claim 11, wherein the point of insertion is determined upon a cursor being located at the point of insertion for a particular amount of time.

18. The method of claim 11, wherein the insertion of the first annotation at point of insertion in the document is presented via the second client computing platform.

19. The method of claim 11, wherein the first client computing platform is a mobile smart phone.

20. The method of claim 11, wherein the second client computing platform is a desktop computer or a laptop computer.

* * * * *